US00PP15588P3

(12) United States Plant Patent
Holland

(10) Patent No.: US PP15,588 P3
(45) Date of Patent: Feb. 22, 2005

(54) LILAC PLANT NAMED 'BAILSUGAR'

(50) Latin Name: *Syringa hybrida*
Varietal Denomination: Bailsugar

(75) Inventor: Neal S. Holland, Harwood, ND (US)

(73) Assignee: Bailey Nurseries, Inc., St. Paul, MN (US)

( * ) Notice: Subject to any disclaimer, the term of this patent is extended or adjusted under 35 U.S.C. 154(b) by 45 days.

(21) Appl. No.: 10/365,435

(22) Filed: Feb. 13, 2003

(65) Prior Publication Data

US 2004/0163151 P1 Aug. 19, 2004

(51) Int. Cl.[7] ..... A01H 5/00

(52) U.S. Cl. ..... Plt./248

(58) Field of Search ..... Plt./248

*Primary Examiner*—Howard J. Locker
(74) *Attorney, Agent, or Firm*—Burns, Doane, Swecker & Mathis, L.L.P.

(57) ABSTRACT

A new and distinct highly ornamental cultivar of *Syringa meyeri*×*Syringa microphylla* is provided. A Lilac plant having a rounded neat compact dwarf growth habit is described. Highly attractive trusses of fragrant purple-lilac blossoms are formed in mid- to late-spring. Good winter hardiness is made possible and the plant has been found to be relatively free of insect and disease problems during observations to date. The plant is particularly well-suited for growing as an ornamental specimens or as a mass planting in the landscape.

2 Drawing Sheets

Figure 1:
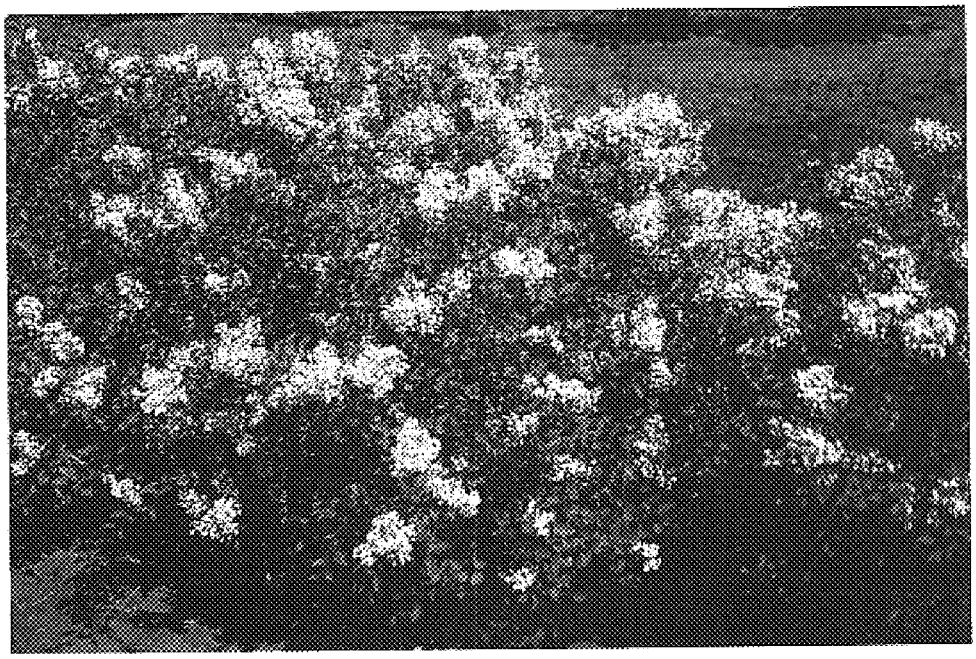

Botanical commercial classification: *Syringa hybrida*/Lilac Shrub.
Varietal denomination: cv. 'Bailsugar'.

SUMMARY OF THE INVENTION

The new Lilac plant of the present invention was created at Harwood, N.D., by the cross of *Syringa meyeri* 'Palibin' (not-patented in the United States) and *Syringa microphylla* 'Superba' (non-patented in the United States). The parentage can be summarized as follows:

'Palibin'×'Superba'.

Seeds from the cross were collected during 1976, were planted, and the resulting plants were observed. A single plant of new cultivar was selected during 1985 in view of its distinctive combination of ornamental characteristics. This plant initially was designated No. 81-3.

It was found that the cultivar of *Syringa meyeri*×*Syringa microphylla* exhibits the following combination of characteristics:

(a) exhibits a rounded neat compact dwarf growth habit,
(b) forms attractive trusses of fragrant purple-lilac blossoms in mid- to late-spring and after many early-flowering shrubs,
(c) is relatively free of insect and disease problems, and
(d) is well-suited for growing as a distinctive ornamental shrub in the landscape.

The new cultivar of the present invention provides a distinctive purple-lilac blossom coloration to the landscape that is displayed in mid- to late-spring after many other shrubs have finished flowering. The purple-lilac blossoms upon maturity fade light red-purple. It can be grown to advantage as a specimen shrub or in a mass planting. The plant is versatile for many uses in the landscape including foundation plantings and informal hedges. The superior hardiness of the *Syringa meyeri* 'Palibin' parent which generally is lacking in the *Syringa microphylla* 'Superba' parent is imparted to the new cultivar of the present invention. However, some winter injury has been observed under wet conditions.

The new cultivar of the present invention can be readily distinguished from the 'Bailbelle' cultivar (U.S. Plant Pat. No. 12,294) and the 'Baildust' cultivar (U.S. Plant patent application Ser. No. 10/158,047, filed May 31, 2002). More specifically, the buds of the 'Bailbelle' cultivar are a distinctive wine color, and buds and blossoms of the 'Baildust' cultivar are of a considerably lighter pale antique pink coloration.

The new cultivar of the present invention was asexually propagated by the use of rooted cuttings and grafting at St. Paul, Minn. during 1992, and the progeny were field planted during 1993. The distinctive characteristics of the new cultivar have been found to be stable and the new cultivar reproduces true to type from one generation to another following such asexual propagation at St. Paul, Minn. and at Yamkill, Oreg.

The new cultivar of the present invention also has been grafted on *Syringa reticulata* to form distinctive small grafted trees.

The new cultivar of the present invention has been named 'Bailsugar'. It is a member of the FAIRYTALE™ Series of Lilac plants that includes the 'Bailbelle' cultivar and the 'Baildust' cultivar, and is being marketed under the SUGAR PLUM FAIRY trademark.

BRIEF DESCRIPTION OF THE PHOTOGRAPHS

The accompanying photographs show, as true as reasonably possible to make the same in color illustrations of this character typical plants of the new cultivar. The plants were propagated by use of rooted cuttings and were photographed when approximately three years of age while growing outdoors during 1998 to 2000 in the field at St. Paul, Minn.

FIG. 1 — shows a mass planting of blossoming plants wherein the neat rounded and compact dwarf growth habit of the new cultivar is exhibited.

Figure 2:
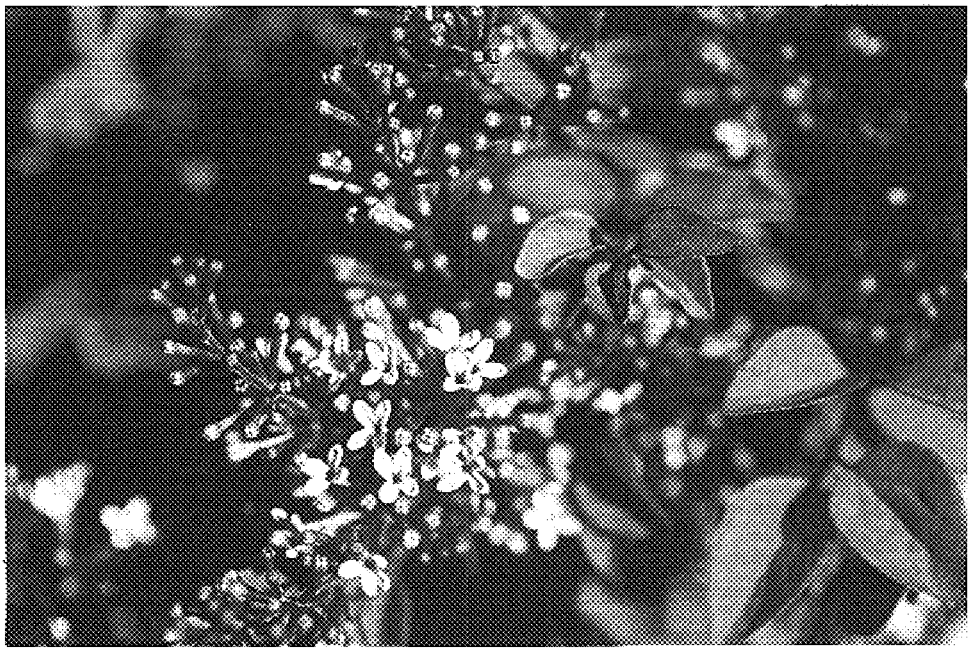

FIG. 2 — shows a closer view of a truss of the purple-lilac buds and blossoms as well as some foliage.

Figure 3:
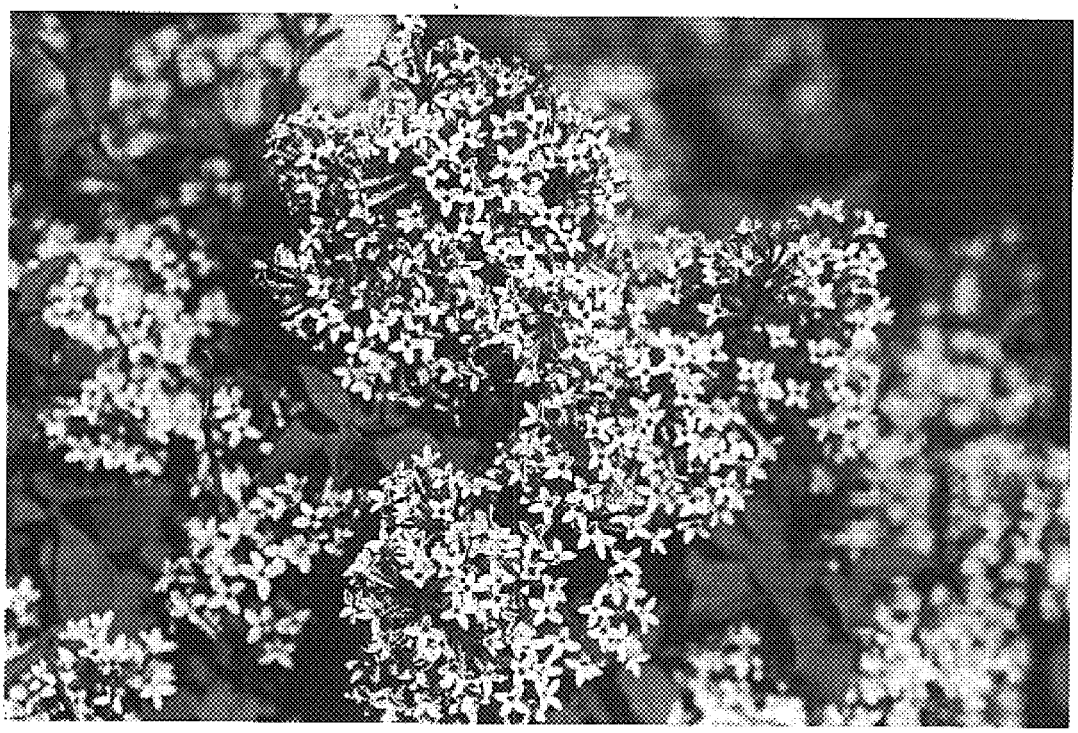

FIG. 3 — shows largely open purple-lilac blossoms with attractive foliage.

Figure 4:
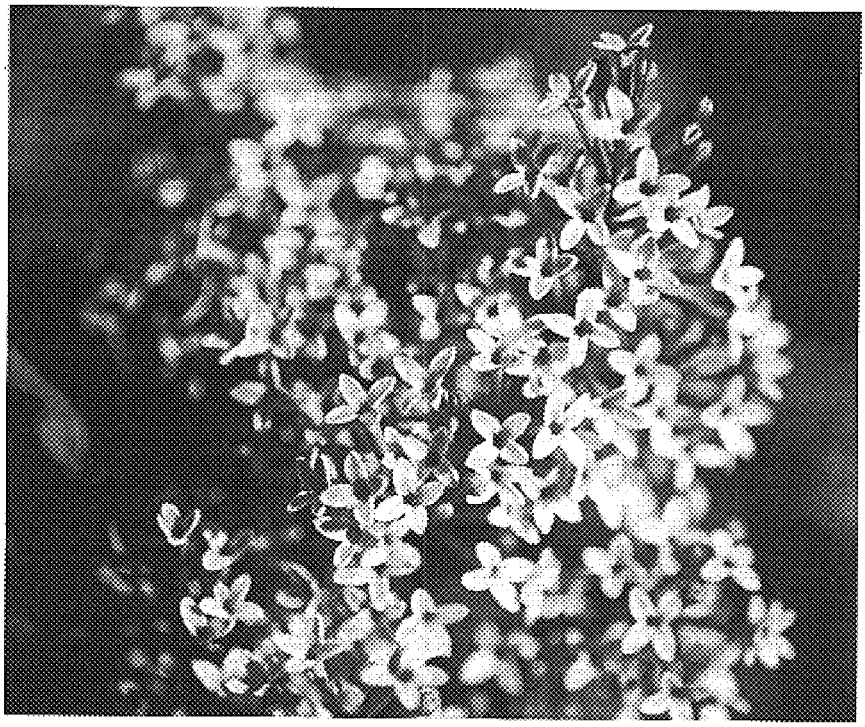

FIG. 4 — shows a closer view of the purple-lilac blossoms.

DETAILED DESCRIPTION

The chart used in the identification of colors is the R.H.S. Colour Chart of The Royal Horticultural Society, London. Common terms are to be accorded their ordinary dictionary significance. The description is based upon the observation of three and five year-old plants propagated by the use of rooted cuttings and growing in the field at St. Paul, Minn.

Botanical classification: *Syringa meyeri*×*Syringa microphylla,* cv. 'Bailsugar'.

Plant:

*Growth habit.*—Neat, compact, rounded dwarf shrub.

*Size.*—Forms a shrub of approximately 5 to 6 feet in height and width.

Bark:

*Texture.*—Rough.

*Color.*—Grey-Brown Group 199B and 199C.

Foliage:

*Leaf shape.*—Elliptic/ovate.

*Arrangement.*—Opposite.

*Leaf apex.*—Acute to obtuse.

*Leaf base.*—Rounded.

*Leaf length.*—Approximately 3 cm on average.

*Leaf width.*—Approximately 2.3 cm on average.

*Leaf surface.*—Non-glossy.

*Leaf margins.*—Entire.

*Color.*—Medium green, Green Group 138A (upper surface) and Green Group 138B (under surface) for young foliage, and Green Group 137A (upper surface) and Green Group 138A (under surface) for adult foliage. This can be compared to Green Group 139A (upper surface) for the adult foliage of the *Syringa meyeri* 'Palibin' parent; Green Group 137A (upper surface) and Green Group 137D (under surface) for the adult foliage of the 'Bailbelle' cultivar, and Green Group 138B (upper surface) and Green Group 138C (under surface) for the 'Baildust' cultivar.

*Petioles.*—Green Group 137C on the upper surface and Green Group 138B on the under surface.

*Stems.*—Green Group 138A (upper surface) and Greyed-Green group 191A (under surface) of young stems, and Greyed-Green Group 197B with highlights of Yellow-Green Group 148B on adult wood.

*Lenticels.*—Commonly are present on stems and measure approximately 0.1 to 0.3 cm, and are Grey-Brown Group 199C in coloration.

Inflorescence:

*Buds.*—In trusses, Beetroot Purple, Red-Purple Group 71A, with margin of Magnolia Purple, Red-Purple Group 70C (upper surface), and Lilac Purple, Red-Purple Group 70B, blending with Magnolia Purple, Red-Purple Group 70C and Campanula Violet, Purple-Violet Group 82C (under surface). The length commonly is 0.2 to 0.6 cm and width is approximately 0.25 cm on average.

*Flower arrangement.*—Densely packed in panicles approximately 7 to 9 cm in length and approximately 5 to 6 cm in width. Each panicle commonly contains approximately 81 blossoms on average.

*Flower configuration.*—Tubular with four petal lobes at the end (as illustrated).

*Flower size.*—Approximately 1.3 cm in length and 0.2 to 0.6 cm in diameter at the widest point.

*Flower color.*—When first opening the petals are Magnolia Purple, Red-Purple Group 70C, blending with Purple-Violet Group 80C at the margin. When blooming the petals are between Red-Purple Group 73C and 73D with Red-Purple Group 69A at the margin (upper surface), and between Red-Purple Group 70B and 70C (under surface). At the end of blooming the petals are Red-Purple Group 69A (upper surface) and Purple Group 78D with highlights of Violet Group 84C (under surface).

*Stamens.*—Two stamens per flower, and near Purple Group 68A with some near White Group 155D in coloration.

*Filaments.*—Red-Purple Group 62D in coloration.

*Anthers.*—Red-Purple Group 64D in coloration.

*Pollen.*—Formed in a moderate quantity and Yellow Group 4B in coloration.

*Pistil.*—Approximately 0.3 cm in length.

*Style.*—Red-Purple Group 68D in coloration.

*Stigma.*—Yellow-Green Group 150D in the absence of pollen and Yellow-Green Group 154D with pollen.

*Calyx.*—Cup-shaped with an entire lobe, rugose, approximately 0.2 cm in size, initially Yellow-Green Group 149D in coloration and changing with maturity to, Phlox Pink, Red-Purple Group 62B, and highlights of Spiraea Red, Red-Purple Group 63D.

*Seeds.*—None found during observations to date.

*Fragrance.*—Spicy lilac.

*Flowering time.*—Mid- to late-May and after many early-flowering shrubs have finished blooming. The new cultivar commonly flowers during the second year from a rooted cutting in the field or in a container. However, a few flowers have been observed during the first year depending upon the time of planting.

*Flower duration.*—Approximately 5 to 7 days on the plant.

Hardiness: Can be grown in U.S.D.A. Hardiness Zone Nos. 3B to 7, and is similar to *Syringa meyeri* 'Palibin' in hardiness. Withstands the winter damage experienced by its *Syringa microphylla* parent which commonly is not reliably hardy in many areas. It has survived winters well during 1976 and 1993 at Harwood, N.D. which is on the border between U.S.D.A. Zone Nos. 3B and 4A. It also generally has wintered well when tested at St. Paul, Minn.; however, there was some winter injury at such location under wet conditions. In contrast the *Syringa microphylla* parent is considered to be hardy in U.S.D.A. Zone No. 5, and cannot winter successfully in the St. Paul, Minn., area over an extended period of time.

Culture: Similar to the *Syringa meyeri* 'Palibin'. Prefers well-drained soil and a sunny growing location. Generally does not well tolerate poorly drained growing conditions.

Vegetation: Vigorous and strong.

Disease/pest resistance: Has proven to be relatively free of disease and insect problems during observations to date. In poorly drained soils root diseases may occur.

Landscape usage: Provides a hardy highly ornamental fragrant shrub having a distinctive blossom coloration that can be grown as a specimen plant or in a mass planting. Can be grown as a foundation planting or as an informal hedge.

I claim:

1. A new and distinct *Syringa meyeri*×*Syringa microphylla* plant having the following combination of characteristics:

(a) exhibits a rounded neat compact dwarf growth habit, (b) forms attractive trusses of fragrant purple-lilac blossoms in mid- to late-spring and after many early-flowering shrubs, (c) is relatively free of insect and disease problems, and (d) is well-suited for growing as a distinctive ornamental shrub in the landscape;

substantially as illustrated and described.

* * * * *